United States Patent
Gemetta et al.

(10) Patent No.: US 11,844,514 B2
(45) Date of Patent: *Dec. 19, 2023

(54) SUTURES AND RELATED MEDICAL DEVICES

(71) Applicant: W. L. Gore & Associates, Inc., Newark, DE (US)

(72) Inventors: Tiffany Gemetta, Flagstaff, AZ (US); Rachel Radspinner, Flagstaff, AZ (US); Elena Ten, Flagstaff, AZ (US); Franklin C. Wetherell, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 137 days.

This patent is subject to a terminal disclaimer.

(21) Appl. No.: 17/403,038

(22) Filed: Aug. 16, 2021

(65) Prior Publication Data
US 2021/0369269 A1 Dec. 2, 2021

Related U.S. Application Data

(63) Continuation of application No. 16/227,954, filed on Dec. 20, 2018, now Pat. No. 11,109,856.
(Continued)

(51) Int. Cl.
*A61B 17/06* (2006.01)
*A61B 17/04* (2006.01)
(Continued)

(52) U.S. Cl.
CPC .... *A61B 17/06166* (2013.01); *A61B 17/0469* (2013.01); *A61F 2/2457* (2013.01); *A61L 17/145* (2013.01); *C08F 114/26* (2013.01); *C08F 214/262* (2013.01); *C08F 216/1408* (2013.01); *A61B 2017/00862* (2013.01);
(Continued)

(58) Field of Classification Search
CPC ...... A61F 2/2466; A61F 2/2457; A61B 17/06; A61B 17/0469; A61B 17/06166; A61B 2017/06171; C08F 114/26
See application file for complete search history.

(56) References Cited

U.S. PATENT DOCUMENTS 3,953,566 A 4/1976 Gore
4,482,516 A 11/1984 Bowman et al.
(Continued)

FOREIGN PATENT DOCUMENTS

CN 106659567 A 5/2017
JP 11-508811 A 8/1999
(Continued)

OTHER PUBLICATIONS

International Preliminary Report on Patentability received for PCT Patent Application No. PCT/US2018/066825, dated Jul. 2, 2020, 12 pages.
(Continued)

*Primary Examiner* — Tuan V Nguyen

(57) ABSTRACT

Various aspects of the present disclosure are directed toward apparatuses, systems, and methods that include a cord that is flexible and elongated defining a length. The cord may include a core having a porous surface and a porosity-reducing element on at least a portion of the core.

20 Claims, 11 Drawing Sheets

Related U.S. Application Data

(60) Provisional application No. 62/608,349, filed on Dec. 20, 2017.

(51) Int. Cl.
  *A61F 2/24* (2006.01)
  *A61L 17/14* (2006.01)
  *C08F 114/26* (2006.01)
  *C08F 214/26* (2006.01)
  *C08F 216/14* (2006.01)
  *A61F 2/00* (2006.01)
  *A61B 17/00* (2006.01)

(52) U.S. Cl.
  CPC ............... *A61B 2017/0619* (2013.01); *A61B 2017/06057* (2013.01); *A61B 2017/06171* (2013.01); *A61B 2017/06176* (2013.01); *A61F 2/2466* (2013.01); *A61F 2002/0081* (2013.01); *A61F 2210/0076* (2013.01); *A61F 2250/0024* (2013.01); *A61L 2400/02* (2013.01); *C08F 2800/20* (2013.01)

(56) References Cited

U.S. PATENT DOCUMENTS

| | | |
|---|---|---|
| 5,450,860 A | 9/1995 | O'Connor |
| 5,708,044 A | 1/1998 | Branca |
| 5,718,251 A | 2/1998 | Gray et al. |
| 6,183,512 B1 | 2/2001 | Howanec et al. |
| 6,541,589 B1 | 4/2003 | Baillie |
| 7,306,729 B2 | 12/2007 | Bacino et al. |
| 7,462,675 B2 | 12/2008 | Chang et al. |
| 7,531,611 B2 | 5/2009 | Sabol et al. |
| 7,635,386 B1 | 12/2009 | Gammie |
| 8,637,144 B2 | 1/2014 | Ford |
| 8,852,213 B2 | 10/2014 | Gammie et al. |
| 8,992,606 B2 | 3/2015 | Ruyra Baliarda |
| 9,139,669 B2 | 9/2015 | Xu et al. |
| 9,204,965 B2 | 12/2015 | Longoria |
| 11,109,856 B2 | 9/2021 | Gemetta et al. |
| 2004/0024448 A1 | 2/2004 | Chang et al. |
| 2004/0122503 A1 | 6/2004 | Campbell et al. |
| 2004/0267313 A1 | 12/2004 | Amery et al. |
| 2006/0041091 A1 | 2/2006 | Chang et al. |
| 2006/0198866 A1 | 9/2006 | Chang et al. |
| 2006/0269754 A1 | 11/2006 | Hayashi et al. |
| 2008/0228272 A1 | 9/2008 | Moaddeb et al. |
| 2009/0318962 A1 | 12/2009 | Spedden et al. |
| 2010/0030241 A1 | 2/2010 | Yeung et al. |
| 2010/0137679 A1 | 6/2010 | Lashinski et al. |
| 2010/0179574 A1 | 7/2010 | Longoria et al. |
| 2010/0305686 A1* | 12/2010 | Cragg ............ A61F 2/07 623/1.35 |
| 2011/0257581 A1* | 10/2011 | Koziczynski ........ A61B 17/06 604/11 |
| 2015/0224231 A1 | 8/2015 | Bruchman et al. |
| 2019/0183489 A1 | 6/2019 | Gemetta et al. |
| 2019/0247185 A1 | 8/2019 | Gassler |

FOREIGN PATENT DOCUMENTS

| | | |
|---|---|---|
| JP | 2017-528205 A | 9/2017 |
| WO | 97/40775 A1 | 11/1997 |
| WO | 2016/028591 A1 | 2/2016 |

OTHER PUBLICATIONS

International Search Report and Written Opinion received for PCT Patent Application No. PCT/US2018/066825, dated Mar. 21, 2019, 16 pages.

Ritchie, Jennifer Lynn; The Material Properties of the Chordae Tendineae of the Mitral Valve: an in Vitro Investigation; Georgia Institute of Technology, Aug. 2004, 219 pages.

\* cited by examiner

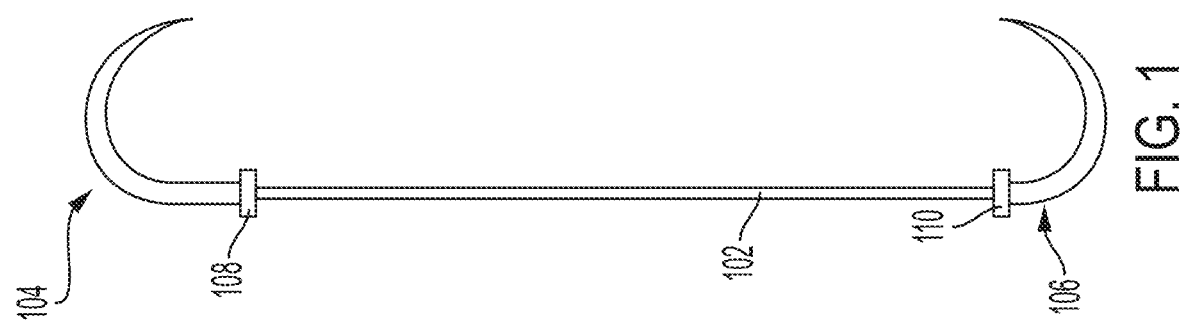
FIG. 1

SUTURES AND RELATED MEDICAL DEVICES

CROSS-REFERENCE TO RELATED APPLICATION

This application is a continuation of U.S. application Ser. No. 16/227,954, filed Dec. 20, 2018, which claims the benefit of Provisional Application No. 62/608,349, filed Dec. 20, 2017, both of which are incorporated herein by reference in their entireties for all purposes.

FIELD

The present disclosure relates generally to embodiments of sutures with improved performance.

BACKGROUND

A suture is a medical device used to hold skin, internal organs, blood vessels, and other tissues of a human or animal body together, tissue of the human body to non-tissue (e.g., a medical device), when they have been severed by injury, incision, surgery, with bone, the like. Similar to other methods of wound closure, utilizing a suture allows an opportunity for the edges of tissue to be held together until healing can occur. Sutures may also be used for cardiovascular surgery, soft tissue approximation, anastomoses of vascular grafts, carotid endarterectomy procedures, ventral hernia repair, inguinal hernia repair, oral surgery, and general surgical suspension procedures. There are various types of sutures with different properties suitable for various uses. Generally, sutures must be strong, biocompatible, and flexible to allow them to be used in stitching and form suitable knots, and are generally elongated cords or threads.

In permanent or long-term implantations, sutures may degenerate, stretch, or otherwise lose physical properties leading to failure. Failure in this sense is any condition of the suture that is detrimental to the intended purpose. Thus, there is a need for improvements to sutures that avoids failure of the suture.

SUMMARY

According to one example ("Example 1"), a suture device includes a cord that is flexible and elongated defining a length, a first end and a second end opposite the first end, the cord including a core extending from the first end to the second end and having a porous surface, the cord further including a porosity-reducing element on at least a portion of the core configured to eliminate a porosity or cover the pores of the surface of the portion of the core.

According to another example ("Example 2"), further to the suture device of Example 1, the porosity-reducing element is a non-permeable film that is wrapped around and coupled to the portion of the core.

According to another example ("Example 3"), further to the suture device of Example 2, the non-permeable film is an ePTFE film having a micro-structure that has smaller pores than a microstructure of the surface of the core.

According to another example ("Example 4"), further to the suture device of any one of Examples 1-3, the porosity-reducing element is an elastomer, elastomeric material, or non-elastomeric TFE-PMVE copolymer coating on the portion of the core rendering the surface of the core at the portion of the core non-porous.

According to another example ("Example 5"), further to the suture device of any one of Examples 1-3, the porosity-reducing element is an elastomer, elastomeric material, or non-elastomeric TFE-PMVE copolymer imbibed into the pores of the portion of the core rendering the surface of the core at the portion of the core non-porous.

According to another example ("Example 6"), further to the suture device of any one of Examples 1-3, the porosity-reducing element is an elastomer or elastomeric material imbibed into the pores of the portion of the core further including a non-elastomeric TFE-PMVE copolymer coating on the portion of the core rendering the surface of the core at the portion of the core non-porous.

According to another example ("Example 7"), further to the suture device of any one of Examples 1-3, the porosity-reducing element is a composite film wrapped around and coupled to the portion of the core, the composite film including: a porous film; and an elastomer, elastomeric material, or non-elastomeric TFE-PMVE copolymer coating on or imbibed into the pores of the porous film rendering the porous film non-porous.

According to another example ("Example 8"), further to the suture device of any one of Examples 1-3, the porosity-reducing element is an elastomer, elastomeric material, or non-elastomeric TFE-PMVE copolymer coating on and imbibed into the pores of the portion of the core rendering the surface of the core at the portion of the core non-porous.

According to another example ("Example 9"), further to the suture device of any one of Examples 4-7, the core includes a fluoropolymer.

According to another example ("Example 10"), further to the suture device of Example 9, the TFE-PMVE copolymer includes from about 40 to about 80 weight percent perfluoromethyl vinyl ether and from about 60 to about 20 weight percent tetrafluoroethylene, or wherein the TFE-PMVE copolymer includes from about 33 to about 39 weight percent perfluoromethyl vinyl ether and respectively from about 72 to about 61 weight percent tetrafluoroethylene, or wherein the TFE-PMVE copolymer includes from about 27 to about 32 weight percent perfluoromethyl vinyl ether and respectively from about 73 to about 68 weight percent tetrafluoroethylene and the TFE-PMVE copolymer is present in pores of the fluoropolymer such that the pores are covered or imbibed.

According to another example ("Example 11"), further to the suture device of Example 9, the TFE-PMVE copolymer includes from about 40 to about 80 weight percent perfluoromethyl vinyl ether and from about 60 to about 20 weight percent tetrafluoroethylene or wherein a TFE-PMVE copolymer includes from about 33 to about 39 weight percent perfluoromethyl vinyl ether and respectively from about 72 to about 61 weight percent tetrafluoroethylene is imbibed into the pores of the portion of the core, and further including a coating of TFE-PMVE copolymer includes from about 27 to about 32 weight percent perfluoromethyl vinyl ether and respectively from about 73 to about 68 weight percent tetrafluoroethylene on the portion of the core rendering the surface of the core at the portion of the core non-porous.

According to another example ("Example 12"), further to the suture device of any one of Examples 4-11, the elastomer or elastomeric material is configured to increase the tackiness of the core for improved knot holding.

According to another example ("Example 13"), further to the suture device of any one of Examples 1-12, the core includes ePTFE.

According to another example ("Example 14"), further to the suture device of any one of claims 1-13, the device also includes a first attachment element at the first end of the cord configured to attach to a first location at a first tissue; and a second attachment element at the second end of the cord configured to attach to a second location at a second tissue.

According to another example ("Example 15"), further to the suture device of Example 14, the composite film is helically wrapped about the core.

According to another example ("Example 16"), further to the suture device of Example 15, the cord includes a length and the composite film is formed of a first portion and a second portion helically wrapped about the core, and the first portion and the second portion are wound in opposite directions along the length of the cord.

According to another example ("Example 17"), further to the suture device of any of Examples 1-16, the core includes ePTFE, and the porosity-reducing element is a TFE-PMVE copolymer that includes from about 40 to about 80 weight percent perfluoromethyl vinyl ether and from about 60 to about 20 weight percent tetrafluoroethylene or a TFE-PMVE copolymer that includes from about 33 to about 39 weight percent perfluoromethyl vinyl ether and respectively from about 72 to about 61 weight percent tetrafluoroethylene is imbibed into the pores of the portion of the core, and further including a coating of TFE-PMVE copolymer that includes from about 27 to about 32 weight percent perfluoromethyl vinyl ether and respectively from about 73 to about 68 weight percent tetrafluoroethylene on the portion of the core rendering the surface of the core at the portion of the core non-porous In Example 18, a chordae tendineae repair or replacement device including the cord of any one of Examples 1-17, the chordae tendineae repair or replacement device also includes a first attachment element coupled to the first end of the cord configured to attach to a first location at a first tissue; and a second attachment element coupled to the second end of the cord configured to attach to a second location at a second tissue.

According to another example ("Example 19"), further to the chordae tendineae repair or replacement device of Example 18, the first attachment element is releasably coupled to a first tissue piercing member that is configured to pierce through tissue, and wherein the second attachment element is releasably coupled to a second tissue piercing member that is configured to pierce through the tissue.

According to another example ("Example 20"), further to the chordae tendineae repair or replacement device of any one of Examples 18-19, at least a first portion of the cord between the first end and the second end is configured to be secured to a second tissue and further including a pledget fixed in position on the first portion and configured to engage the second tissue According to another example ("Example 21"), a method for treating a defective mitral or tricuspid valve includes percutaneously accessing a region of a heart with a catheter-based device; and repairing a cardiac valve by use of the device, wherein the repairing includes augmenting or replacing at least one chordae tendineae, wherein the replaced chordae tendineae includes a suture device of any of Examples 1-20.

According to another example ("Example 22"), a method for reducing or avoiding calcification of sutures utilized as replacement chordae tendineae includes percutaneously accessing a region of a heart with a catheter-based device; and repairing a cardiac valve by use of said device, wherein the repairing includes augmenting or replacing at least one chordae tendineae, wherein the replaced chordae tendineae includes a suture device of any of Examples 1-20.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 1 is an illustration of a suture device in accordance with an embodiment;

DETAILED DESCRIPTION

Figure 2:
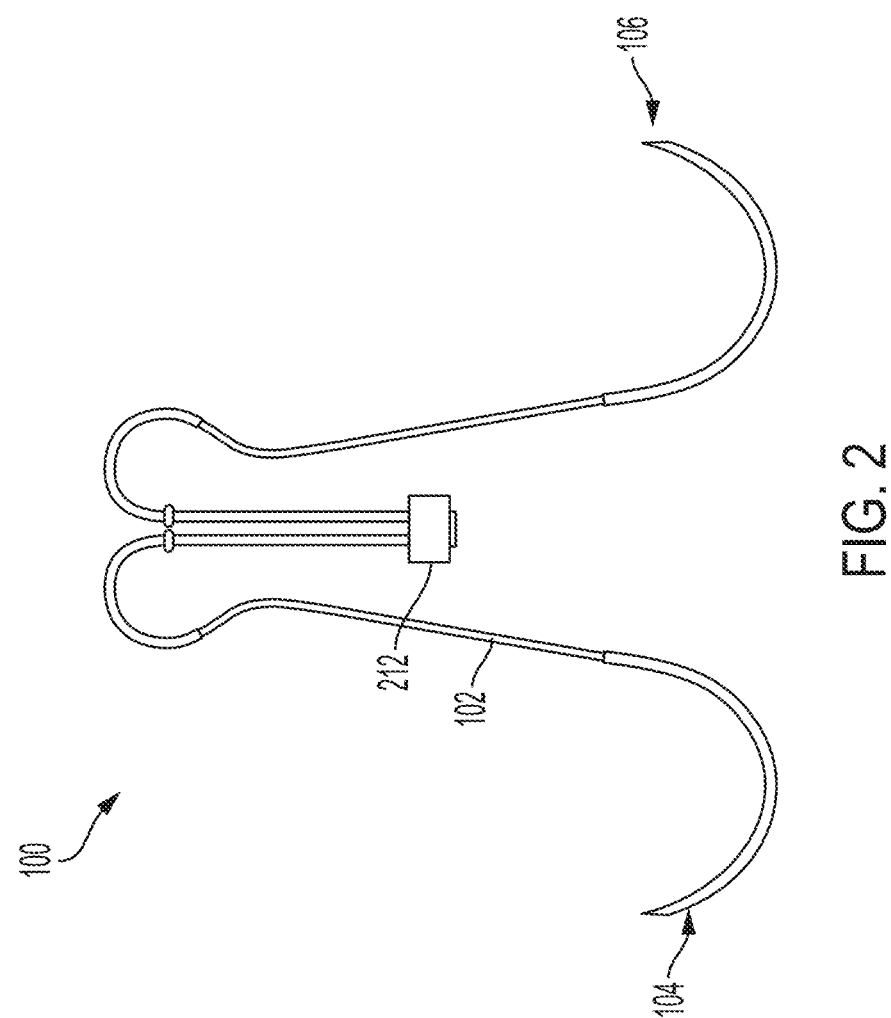
FIG. 2 is an illustration of another suture device in accordance with an embodiment.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward sutures having improved properties. The sutures may be utilized in and around the heart, in connecting tissue, or sealing wounds. The sutures, for example, may be used in chordae tendineae repair or replacement procedures. The sutures, as discussed in detail below, may include improved knot holding capacity (knot strength and knot security) to allow for faster knot tying and smaller knots, and optimized surface characteristics for varied applications (e.g., non-porous surface for applications within the preperitoneal space to prevent adhesion, or porous surface where tissue ingrowth is desired).

The sutures (e.g., tissue connectors) discussed herein may be used in devices, methods, and systems and may be configured to lessen the opportunity for rupture of the suture. In certain uses, such as for chordae tendineae repair or replacement, rupture of the suture can be a failure mode. In certain instances and as discussed in further detail below, the mechanical properties of the sutures are designed to avoid breakage or rupture in vivo. Porous sutures are prone to calcium and other blood components being deposited in the pores leading to stiffening and other material property changes that may lead to failure. Failure in this sense is any condition of the suture that is detrimental to the intended purpose. Calcification of the sutures may lead to rupture of the sutures, which may result in injury to tissue or reduced heart valve function (e.g., when used for chordae tendineae repair or replacement). Calcification can stiffen the suture and might act as stress concentrator that may eventually lead to a suture failure/rupture. Therefore, preventing proteinaceous fluids from penetrating and staying within the pores of the suture can at least delay the onset of mineralization (e.g., calcification).

In addition, some embodiments of sutures discussed herein are soft, flexible and compressible. As a result, the sutures minimize tissue irritation and prevent leaks around the tissue into which the sutures are arranged. Further, if knotting of the sutures is required, some sutures embodiments are provided with surface characteristics that are operable to better hold a knot while maintaining the low surface friction to allow individual throws to slide easily for precise knot positioning.

As used herein, sutures may include a monofilament or multifilament polymer or natural fibers. A monofilament suture is one comprising a single fiber that runs the entire length of the suture. A multifilament suture comprises multiple fibers that run the entire length of the suture. A multifilament suture may comprise a plurality of monofilaments that are twisted or braided together, or a bunch of fibers that are twisted or braided together. Further, a multifilament suture may comprise a plurality of twisted together fibers, itself twisted together. Additionally, a multifilament suture may comprise a core comprising a monofilament or multifilament that runs the length of the cord that is surrounded by other monofilaments or multifilaments or film, as in a film wrap.

Embodiments described herein are referred to as a composite suture. A composite suture may be a monofilament or multifilament suture that further comprises an elastomer, elastomeric, or non-elastomeric TFE-PMVE copolymer that either coats a core of the suture and/or is imbibed into a porous core of the suture. In addition, the composite suture may be a unitary structure comprising an elastomer, elastomeric, or non-elastomeric polymer.

Embodiments described herein can comprise a composite film or porosity-reducing element that is wrapped and coupled to a core. A porosity-reducing element is an ePTFE membrane that further comprises an elastomer, elastomeric, or non-elastomeric TFE-PMVE copolymer that either coats the membrane (e.g., an ePTFE core, silicone, urethane, or other similar material) and/or is imbibed into a porous structure of the membrane. As used herein, the porosity-reducing element may be used as a wrap, such as to wrap a monofilament or multifilament suture core to form a composite suture as described herein.

TFE-PMVE copolymer comprising from about 40 to about 80 weight percent perfluoromethyl vinyl ether and respectively from about 20 to about 60 weight percent tetrafluoroethylene, for purposes of this disclosure, is considered an "elastomer."

TFE-PMVE copolymer comprising from about 33 to about 39 weight percent perfluoromethyl vinyl ether and respectively from about 67 to about 61 weight percent tetrafluoroethylene, for purposes of this disclosure, is considered an "elastomeric material."

TFE-PMVE copolymer comprising from about 27 to about 32 weight percent perfluoromethyl vinyl ether and respectfully from about 73 to about 68 weight percent tetrafluoroethylene, for purposes of this disclosure, is considered not an elastomer or elastomeric material and will be referred to herein as "non-elastomeric TFE-PMVE copolymer." This non-elastomeric copolymer, as compared to the above elastomer and elastomeric TFE-PMVE copolymer, has the unique property of being less tacky and is able to pass a tack test as provided herein. It is appreciated that the degree of tackiness may be chosen for a particular purpose. A more tacky suture may have an improved knot-holding ability whereas a less tacky or non-tacky suture may have better handling properties in a transcatheter procedure. This non-elastomeric TFE-PMVE copolymer, as compared to the above elastomer and elastomeric TFE-PMVE copolymer, has the unique property of exhibiting less tackiness.

In accordance with an embodiment of a composite suture, a core of a monofilament suture is coated with an elastomer, elastomeric material, or non-elastomeric TFE-PMVE copolymer. In accordance with an embodiment, the core of the suture is dip-coated into the TFE-PMVE copolymer to affect a coating onto the suture. In accordance with another embodiment, the core of the suture is dip-coated into the TFE-PMVE copolymer and further processed under heat and/or pressure to affect a coating and at least partially imbibing the TFE-PMVE copolymer into pores of the core of the suture. In accordance with another embodiment, the core of the suture is wrapped with a film of TFE-PMVE copolymer and further processed under heat and/or pressure to affect a coating and/or at least partially imbibing the TFE-PMVE copolymer into pores of the suture. In accordance with another embodiment, the core of the suture is wrapped with a second film of non-elastomeric TFE-PMVE copolymer and further processed under heat and/or pressure to affect a coating of the non-elastomeric TFE-PMVE copolymer onto the suture. In this embodiment, the non-elastomeric TFE-PMVE copolymer coating significantly reduces the possibility of the pores of the porous core of the suture, in one embodiment an expanded fluoropolymer suture, from receiving fluids that may result in calcium deposits.

In accordance with an embodiment of a core of a composite suture, a multifilament suture, either as a whole or each of the individual monofilaments or fibers that comprise the multifilament suture, is coated with an elastomer, elastomeric, or non-elastomeric TFE-PMVE copolymer. In accordance with an embodiment, the multifilament suture or each of the individual monofilaments or fibers that comprise the multifilament suture, is dip-coated into the TFE-PMVE copolymer to affect a coating onto the suture. In accordance with another embodiment, the suture or each of the individual monofilaments or fibers that comprise the multifilament suture, is dip-coated into the TFE-PMVE copolymer and further processed under heat and/or pressure to affect a coating and at least partially imbibing the TFE-PMVE copolymer into pores of the suture or the pores of each of the individual monofilaments or fibers that comprise the multifilament suture. In accordance with another embodiment, the suture is wrapped with a film of TFE-PMVE copolymer and further processed under heat and/or pressure to affect a coating and at least partially imbibing the TFE-PMVE copolymer into pores of the suture. In accordance with another embodiment, the suture or each of the individual monofilaments or fibers that comprise the multifilament suture, is wrapped with a second film of non-elastomeric TFE-PMVE copolymer and further processed under heat and/or pressure to affect a coating of the non-elastomeric TFE-PMVE copolymer onto the suture or each of the individual monofilaments or fibers that comprise the multifilament suture. In this embodiment, the non-elastomeric TFE-PMVE copolymer coating significantly reduces the possibility of the pores of the porous suture or each of the individual monofilaments or fibers that comprise the multifilament suture, in one embodiment an expanded fluoropolymer suture, from being exposed to or opening up to receive fluids that may lead to calcium deposits or other blood components due, in part, to any creep of an elastomer or elastomeric TFE-PMVE copolymer material in the pores of the suture that may occur over time being exposed to high-cycle flexure.

FIG. 1 is an illustration of an example suture device 100 in accordance with an embodiment. In certain instances, the suture device 100 may include a composite suture, also referred herein as a cord 102, a first tissue piercing member 104 arranged at one end of the cord 102, and a second tissue piercing member 106 arranged at the other end of the cord 102.

The first tissue piercing member 104 and the second tissue piercing member 106 may be attached to the cord 102. In addition, the first tissue piercing member 104 and the second tissue piercing member 106 may each be configured to pierce through heart tissue. In certain instances, the first tissue piercing member 104 and the second tissue piercing member 106 are releasably attached or coupled to the cord 102. In instances where the first tissue piercing member 104 and the second tissue piercing member 106 are releasably attached or coupled to the cord 102, the first tissue piercing member 104 and the second tissue piercing member 106 may be removed after the cord 102 is aligned within a patient.

In certain instances, the suture device 100 may include a cord 102, a first tissue piercing member 104 arranged at one end of the cord 102, and a second tissue piercing member 106 arranged at the other end of the cord 102.

The first tissue piercing member 104 and the second tissue piercing member 106 may be attached to the cord 102. In addition, the first tissue piercing member 104 and the second tissue piercing member 106 may each be configured to pierce through heart tissue. In certain instances, a first attachment element 108 may be coupled or attached to one end of the cord 102 and a second attachment element 110 may be coupled or attached to the other end of the cord 102. The first attachment element 108 and the second attachment element 110 are configured to attach the cord 102 to the tissue of the heart. The first attachment element 108 and the second attachment element 110 may be anchors that pierce the tissue and retain the cord 102 between a first location and a second location with the first attachment element 108 and the second attachment element 110 piercing and retaining at a surface of or within the tissue at, respectively, the first location and the second location. The first attachment element 108 and the second attachment element 110 may be barbs, fixation helixes, or any similar structure.

Figure 10:
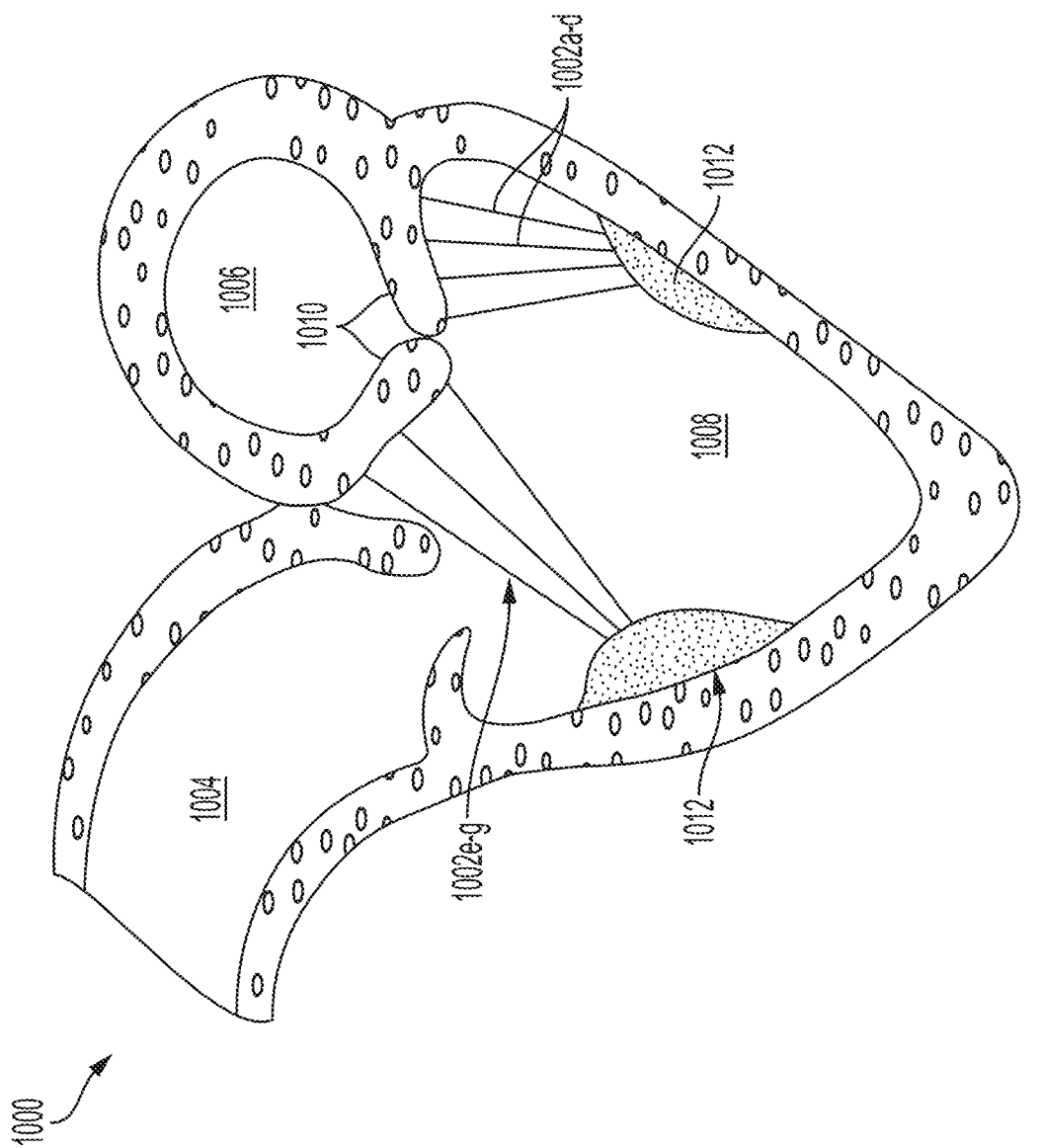
FIG. 10 is an illustration of a patient's heart with chordae tendineae, papillary muscles, mitral valve leaflets and suture devices in accordance with an embodiment.

In certain instances, the cord 102 may be used for treating a defective mitral or tricuspid valve. In these such instances, a region of a heart (e.g., an apical region) is percutaneously accessed with a catheter-based device. At least one chordae tendineae may be repaired or replaced (e.g., as shown in FIG. 10). In certain instances, the cord 102 (e.g., tissue connector) includes a generally circular cross-section. In other instances, the cord 102 may be wrapped about a circumference of the heart or valve annulus to ensure closure of a valve that is experiencing regurgitation. In these instances, the cord 102 compresses the heart or valve annulus to ensure that the leaflets of the valve fully close. The cord 102 may be used for reducing or avoiding calcification of sutures utilized as replacement chordae tendineae as described in further detail below.

In certain instances, the cord 102 is flexible and includes a porosity-reducing element (e.g., as explained in further detail with reference to FIG. 3). Multiple types of fluoropolymer and multiple types of porosity-reducing elements or composite films can be combined while within the spirit of the present embodiments. It should also be readily appreciated that the porosity-reducing element or composite film can include multiple elastomers, multiple types of non-elastomeric components, such as inorganic fillers, therapeutic agents, radiopaque markers, and the like while within the spirit of the present embodiments. The porosity-reducing element may be wrapped and coupled to a core.

In one embodiment, described in greater detail below, failure of the cord 102 was significantly decreased by adding a relatively high-percentage of a relatively lower strength elastomer, elastomeric, or non-elastomeric TFE-PMVE copolymer (e.g., a porosity-reducing element) to pores of a fluoropolymer suture core of the cord 102. Surprisingly, in some embodiments wherein porous fluoropolymer membranes are imbibed with elastomer, elastomeric, or non-elastomeric TFE-PMVE copolymer the presence of the elastomer, elastomeric, or non-elastomeric TFE-PMVE copolymer increased overall thickness of the suture, the resulting increased thickness of the fluoropolymer members due to the addition of the elastomer, elastomeric, or non-elastomeric TFE-PMVE copolymer, surprisingly, did not significantly hinder or diminish flexibility yet improved resistance to calcification. The imbibing of the pores of the expanded fluoropolymer membrane with elastomer, elastomeric material and non-elastomeric material can be performed by a variety of methods known to those skilled in the art.

In one embodiment, the composite suture or film wrap includes an expanded fluoropolymer material made from porous ePTFE, for instance as generally described in U.S. Pat. No. 7,306,729. The expandable fluoropolymer, used to form the expanded fluoropolymer suture or film wrap described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

In one embodiment, the porosity-reducing element that is combined with the ePTFE is a thermoplastic copolymer of tetrafluoroethylene (TFE) and perfluoromethyl vinyl ether (PMVE). The material is combined with the expanded fluoropolymer core surface such that the material occupies substantially all of the void space or pores within the expanded fluoropolymer core surface. This filling of the pores of the expanded fluoropolymer core surface with elastomer can be performed by a variety of methods as discussed in further detail below. In another embodiment, the non-elastomeric material that is combined with the ePTFE is a thermoplastic copolymer of tetrafluoroethylene (TFE) and perfluoromethyl vinyl ether (PMVE), such as described above. The material is combined with the expanded fluoropolymer substrate surface such that the material occupies substantially all of the void space or pores within the expanded fluoropolymer substrate surface. This filling of the pores of the expanded fluoropolymer core surface with non-elastomeric TFE-PMVE copolymer can be performed by a variety of methods as discussed in further detail below.

In certain instances, the TFE and PMVE components of the TFE-PMVE copolymer are presented in weight percentage (wt %). For reference, the wt % of PMVE of 40, 33-39, and 27-33 corresponds to a mol % of 29, 23-28, and 18-22, respectively. In certain instances, the TFE-PMVE copolymer is an elastomer, elastomeric, or non-elastomeric.

Embodiments of the expanded fluoropolymer membrane combined with TFE-PMVE copolymer that exhibits elastomeric, and non-elastomeric properties provides performance attributes required for use in high-cycle flexural implant applications, such as chordae tendineae repair or replacement, in at least several significant ways. For example, the addition of TFE-PMVE copolymer that exhibits elastomer, elastomeric, and non-elastomeric properties improves the fatigue performance of the cord 102 by eliminating or reducing the stiffening observed with ePTFE-only materials. In addition, it reduces the likelihood that the material will undergo permanent set deformation, such as wrinkling or creasing, that could result in compromised performance. In one embodiment, the TFE-PMVE copolymer that exhibits elastomer, elastomeric, or non-elastomeric properties occupies substantially all of the pore volume or space within the porous structure of the expanded fluoropolymer membrane. In another embodiment the TFE-PMVE copolymer that exhibits elastomeric, or non-elastomeric properties is present in substantially all of the pores of the at least one fluoropolymer layer. Having TFE-PMVE copolymer that exhibits elastomer, elastomeric, or non-elastomeric properties filling the pore volume or present in substantially all of the pores reduces the space in which foreign materials can be undesirably incorporated into the core of the suture.

An example of such foreign material entering into pores or spaces that may open up in the composite suture comprising a porous expanded fluoropolymer monofilament(s) having an elastomer or elastomeric TFE-PMVE copolymer in the pores, is calcium. If calcium becomes incorporated into the composite suture, as used in a cord 102, for example, mechanical damage can occur during cycling, thus leading to degradation in structural characteristics.

A layer or coating of TFE-PMVE copolymer comprising from about 27 to about 32 weight percent perfluoromethyl vinyl ether and respectively from about 73 to about 68 weight percent tetrafluoroethylene significantly reduces the possibility of the pores of the porous structure of the expanded fluoropolymer suture from receiving, or opening up to receive calcium deposits or other blood components due, in part, to the elastomer or elastomeric material in the pores of the expanded fluoropolymer suture.

A material according to one embodiment includes an expanded fluoropolymer suture and an elastomeric material within the pores of the expanded fluoropolymer, and further comprising a coating of TFE-PMVE copolymer comprising from about 27 to about 32 weight percent perfluoromethyl vinyl ether and from about 73 to about 68 weight percent tetrafluoroethylene. It should be readily appreciated that multiple types of fluoropolymer sutures and multiple types of elastomer, elastomeric, or non-elastomeric TFE-PMVE copolymer can be combined for use with the cord 102 while within the spirit of the present disclosure.

TFE-PMVE copolymer comprising from about 27 to about 32 weight percent perfluoromethyl vinyl ether and respectfully from about 73 to about 68 weight percent tetrafluoroethylene, for purposes of this disclosure, is considered not an elastomer or elastomeric material and will be referred to herein as "non-elastomeric TFE-PMVE copolymer." Being non-soluble, the non-elastomeric TFE-PMVE copolymer can be thermally formed, as with extrusion, into a sheet suitable for coupling to the suture or to individual monofilaments of a multifilament suture.

In an embodiment, a method of coating a composite suture or each of the individual monofilaments or fibers that comprise the multifilament suture comprising expanded fluoropolymer membrane imbibed with elastomer or elastomeric material, with a non-elastomeric TFE-PMVE copolymer comprising from about 27 to about 32 weight percent perfluoromethyl vinyl ether and respectively from about 73 to about 68 weight percent tetrafluoroethylene includes the steps of bringing the composite suture or each of the individual monofilaments or fibers that comprise the multifilament suture into contact with a sheet of the non-elastomeric TFE-PMVE copolymer under conditions of heat and/or pressure that allow the non-elastomeric TFE-PMVE copolymer to couple with the composite suture or each of the individual monofilaments or fibers that comprise the multifilament suture.

By way of example, but not limited thereto, a 1.5 μm thick layer of non-elastomeric TFE-PMVE copolymer, per the above, was coupled to an ePTFE membrane that was imbibed with elastomeric TFE-PMVE copolymer comprising from about 33 to about 39 weight percent perfluoromethyl vinyl ether and respectively from about 72 to about 61 weight percent tetrafluoroethylene, by sandwiching the membrane between two non-elastomeric TFE-PMVE copolymer layers under 900 kPa pressure and 165° C. temperature for 15 minutes which affected a bond between the components.

In addition to porous membranes or monofilaments, it is appreciated that non-porous membrane or monofilaments may be coated with the non-elastomeric TFE-PMVE copolymer comprising from about 27 to about 32 weight percent perfluoromethyl vinyl ether and respectively from about 73 to about 68 weight percent tetrafluoroethylene suitable for a particular purpose. Among other things, it is appreciated that the non-elastomeric TFE-PMVE copolymer provides a non-tacky material that resists adhesion when the cord 102 is arranged in a delivery configuration prior to transcatheter placement. It is appreciated that medical devices, such as, but not limited to, the cord 102, provided with non-tacky surfaces have particular handling advantages over those having a tacky or sticky surface.

In accordance with an embodiment, the composite suture comprises an elastomeric material comprising the TFE-PMVE copolymer having from about 33 to about 39 weight percent perfluoromethyl vinyl ether and respectively from about 67 to about 61 weight percent tetrafluoroethylene and an ePTFE monofilament or multifilament suture. In an embodiment, the TFE-PMVE copolymer is present in the pores of the ePTFE monofilament or multifilament suture.

In accordance with another embodiment, the composite monofilament or multifilament suture comprises elastomer material comprising from about 40 to about 80 weight percent perfluoromethyl vinyl ether and respectively from about 60 to about 20 weight percent tetrafluoroethylene and a fluoropolymer such as ePTFE or PTFE membrane.

Other biocompatible polymers which may be suitable for use in the cord 102 embodiments may include but not be limited to the groups of nylon, urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

FIG. 2 is an illustration of another example suture device 100 in accordance with an embodiment. In certain instances, the suture device 100 may include a cord 102, a first tissue piercing member 104 arranged at one end of the cord 102, and a second tissue piercing member 106 arranged at the other end of the cord 102. The first tissue piercing member 104 and the second tissue piercing member 106 may be attached or releasably coupled to the cord 102. In addition, the first tissue piercing member 104 and the second tissue piercing member 106 may each be configured to pierce through heart tissue.

In certain instances, the cord 102 may be used for treating a defective mitral or tricuspid valve. In these such instances, an apical region of a heart is percutaneously accessing with a catheter-based device. The cardiac valve is repaired by augmenting or replacing at least one chordae tendineae (e.g., as shown in FIG. 10). The replaced chordae tendineae may include the cord 102, which can be referred to as a tissue connector due to the cord 102 connecting two portions of the heart tissue that the repaired chordae tendineae connected. In certain instances, the cord 102 includes a flexible cord with a generally circular cross-section. In certain instances, the cord 102 may also include a pledget 212 (or other similar wound stopping structure) that is fixed in position on the cord 102. The pledget 212 may protect tissue from tearing. The pledget 212 or similar stop device being installed on the end of the cord 102 allows for the cord 102 to be pulled entirely through the tissue until the pledget 212 is reached. The pledget 212 or stop may then be left in this position or be sewn into place for added security.

Figure 3:
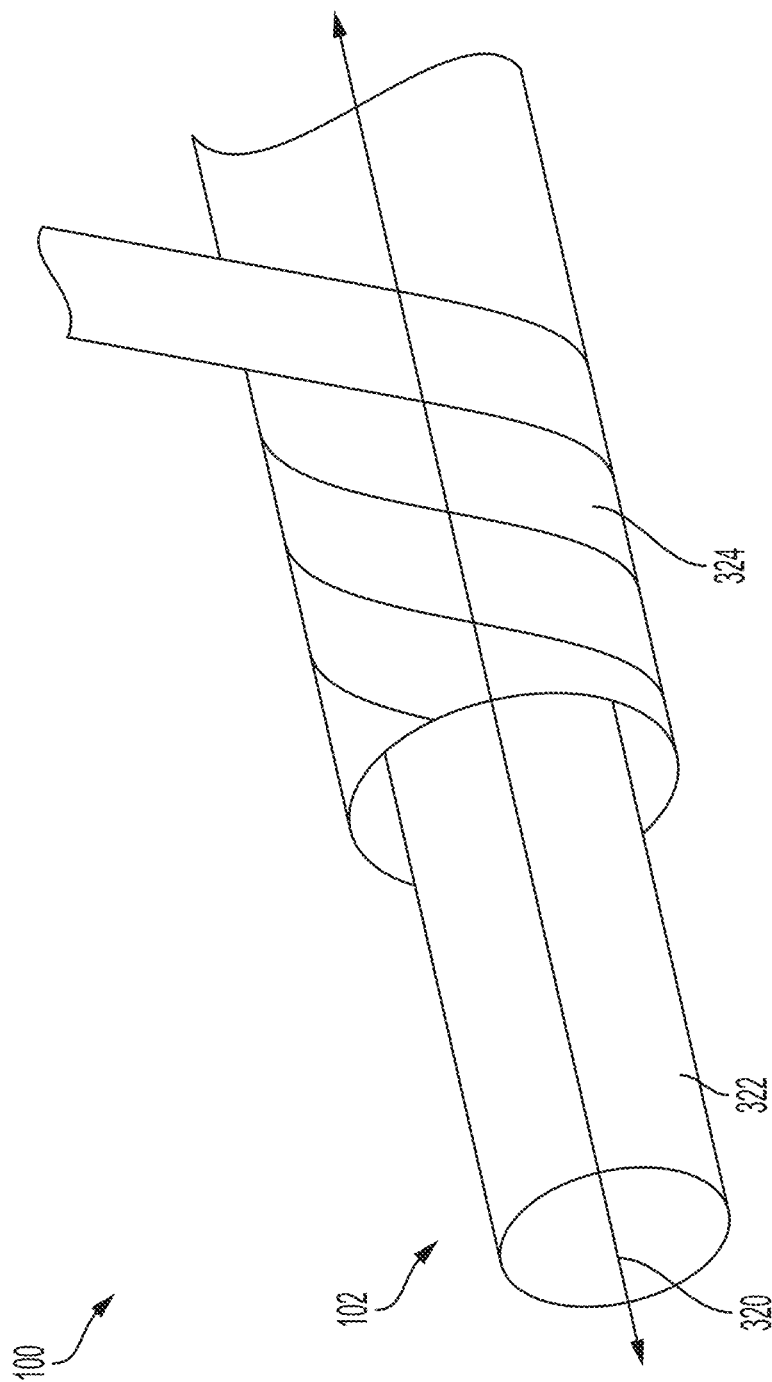
FIG. 3 is an illustration of a suture device in accordance with an embodiment.

FIG. 3 is an illustration of an example suture device 100 in accordance with an embodiment. The suture device 100 includes a cord 102 with a longitudinal axis 320. As shown in FIG. 3, the cord 102 includes a monofilament or multi-filament suture in the form of a core 322 having a primary strength oriented with the longitudinal axis 320. In certain instances, the core 322 extends from a first end to a second end of the cord 102 and includes a porous surface. The cord 102 further includes a porosity-reducing element 324 on at least a portion of the core 322 that is configured to eliminate a porosity or cover the pores of the surface of the portion of the core 322. The porosity-reducing element 324 (e.g., a porous expanded fluoropolymer film with an elastomer, elastomeric, or non-elastomeric TFE-PMVE copolymer within the pores) may be coupled with at least a portion of the core 322. In certain instances, the porosity-reducing element 324 is a non-permeable film that is wrapped around and coupled to the portion of the core 322. In addition, the non-permeable film is an ePTFE film having a microstructure that has smaller pores than a microstructure of the surface of the core 322.

In addition, the strength of the core 322 may be oriented with the longitudinal axis 320 and is a primary strength of the core 322. The core 322 may be a fluoropolymer material having fibrils. A majority or greater of the fibrils of the core 322 may be oriented with the longitudinal axis 320 to orient the primary strength of the core 322 therewith.

In certain instances, the porosity-reducing element 324 may be a tape that is coupled to the surface of the core 322.

As shown in FIG. 3, the porosity-reducing element 324 is helically wrapped about the core 322. In other instances, the porosity-reducing element 324 may be rolled about the core 322 similar to joint edges of the porosity-reducing element 324 together to seal the core 322.

As discussed in detail above with reference to FIG. 3, the core 322 may be formed of a porous expanded fluoropolymer (e.g., ePTFE). In certain instances, the cord 102 may include a TFE/PMVE copolymer within the pores of the porous expanded fluoropolymer core. A TFE/PMVE copolymer can include from about 40 to about 80 weight percent perfluoromethyl vinyl ether and from about 60 to about 20 weight percent tetrafluoroethylene. An elastomeric copolymer can include TFE-PMVE copolymer comprising from about 33 to about 39 weight percent perfluoromethyl vinyl ether and respectively from about 72 to about 61 weight percent tetrafluoroethylene.

In certain instances, the porosity-reducing element 324 is an elastomer, elastomeric material, or non-elastomeric TFE-PMVE copolymer coating on a portion of the core 322 rendering the surface of the core 322 at the portion of the core 322 non-porous. In addition, the porosity-reducing element 324 may be an elastomer, elastomeric material, or non-elastomeric TFE-PMVE copolymer imbibed into the pores of a portion of the core 322 rendering the surface of the core 322 at the portion of the core 322 non-porous. In certain instances, the porosity-reducing element 324 is an elastomer or elastomeric material imbibed into the pores of a portion of the core 322 further including a non-elastomeric TFE-PMVE copolymer coating on the portion of the core 322 rendering the surface of the core 322 at the portion of the core 322 non-porous.

In certain instances, the core 322 includes a fluoropolymer. Further, the TFE-PMVE copolymer of the porosity-reducing element 324 may include from about 40 to about 80 weight percent perfluoromethyl vinyl ether and from about 60 to about 20 weight percent tetrafluoroethylene, or the TFE-PMVE copolymer may include from about 33 to about 39 weight percent perfluoromethyl vinyl ether and respectively from about 72 to about 61 weight percent tetrafluoroethylene, or the TFE-PMVE copolymer may include from about 27 to about 32 weight percent perfluoromethyl vinyl ether and respectively from about 73 to about 68 weight percent tetrafluoroethylene and the TFE-PMVE copolymer which is present in pores of the fluoropolymer such that the pores are covered or imbibed.

In certain instances, the TFE-PMVE copolymer of the porosity-reducing element 324 may include from about 40 to about 80 weight percent perfluoromethyl vinyl ether and from about 60 to about 20 weight percent tetrafluoroethylene or a TFE-PMVE copolymer may include from about 33 to about 39 weight percent perfluoromethyl vinyl ether and respectively from about 72 to about 61 weight percent tetrafluoroethylene which is imbibed into the pores of the portion of the core 322, and there may also be a coating of TFE-PMVE copolymer that includes from about 27 to about 32 weight percent perfluoromethyl vinyl ether and respectively from about 73 to about 68 weight percent tetrafluoroethylene on the portion of the core 322 rendering the surface of the core 322 at the portion of the core 322 non-porous.

In certain instances, the core 322 includes ePTFE and the porosity-reducing element 322 is a TFE-PMVE copolymer that includes from about 40 to about 80 weight percent perfluoromethyl vinyl ether and from about 60 to about 20 weight percent tetrafluoroethylene or a TFE-PMVE copolymer includes from about 33 to about 39 weight percent perfluoromethyl vinyl ether and respectively from about 72 to about 61 weight percent tetrafluoroethylene which is imbibed into the pores of the portion of the core 322, and also includes a coating of TFE-PMVE copolymer that includes from about 27 to about 32 weight percent perfluoromethyl vinyl ether and respectively from about 73 to about 68 weight percent tetrafluoroethylene on the portion of the core 322 rendering the surface of the core 322 at the portion of the core 322 non-porous.

Figure 4:
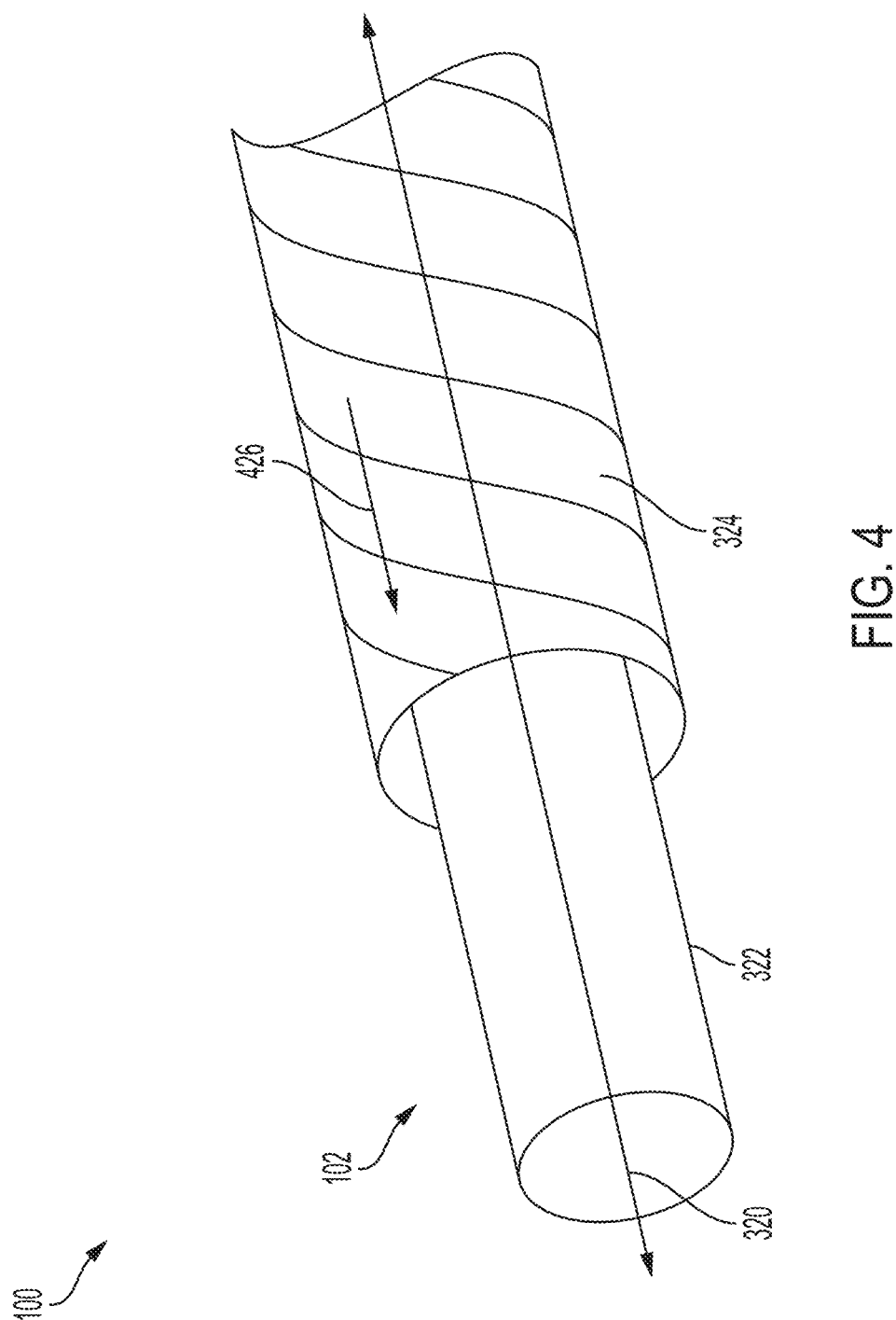
FIG. 4 is an illustration of another suture device in accordance with an embodiment.

FIG. 4 is an illustration of another example suture device 100 in accordance with an embodiment. The suture device 100 includes a cord 102 with a longitudinal axis 320, with the cord 102 including a core 322 having a strength 426 oriented with the longitudinal axis 320 of the cord 102. In addition, a porosity-reducing element 324 may be coupled to or with at least a portion of the core 322. The porosity-reducing element 324 (e.g., a porous expanded fluoropolymer film with an elastomer, elastomeric, or non-elastomeric TFE-PMVE copolymer within the pores) may be configured to reduce porosity of the surface of the cord 102.

In certain instances, the porosity-reducing element 324 is coupled to the core 32, as is shown in FIG. 4. In addition, the strength of the core 322 may be oriented with the longitudinal axis 320 and is a primary strength of the core 322. As shown in FIG. 4, the porosity-reducing element 324 covers the core 322. The porosity-reducing element 324 may be wrapped about the core 322 (which may be porous), and then further processed under conditions of heat and/or pressure that couples the porosity-reducing element 324 to the core 322.

Figure 5:
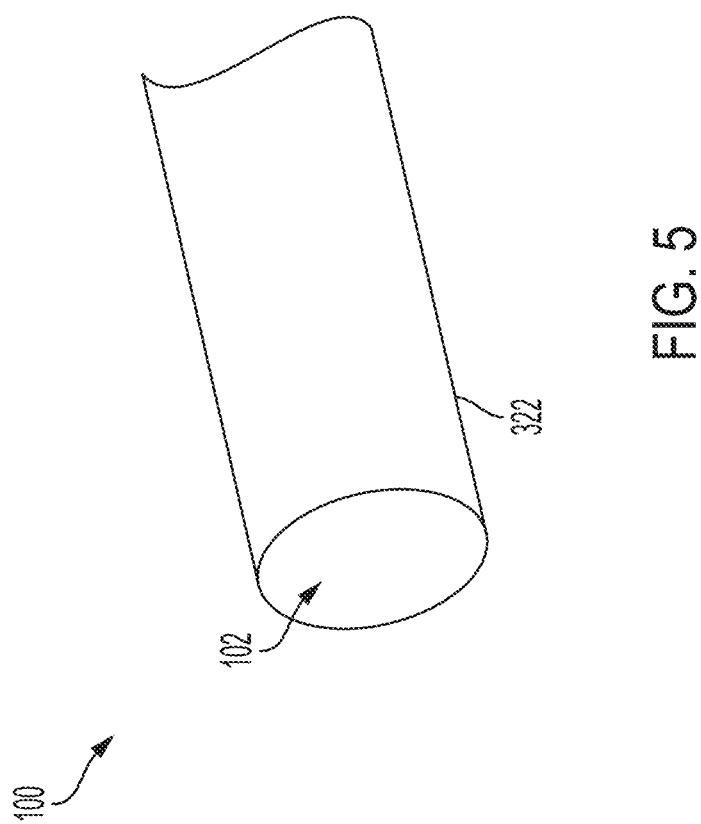
FIG. 5 is an illustration of yet another suture device in accordance with an embodiment.

FIG. 5 is an illustration of yet another example suture device 100 in accordance with an embodiment. The suture device 100 includes a cord 102 having a core 322. The core 322 may be a unitary cord 102 having a porosity-reducing element 324 (e.g., composite film including an elastomer, elastomeric, or non-elastomeric TFE-PMVE copolymer or a composite film including elastomer, elastomeric, or non-elastomeric TFE-PMVE copolymer and ePTFE membrane) combined with the core 322. In certain instances, the porosity-reducing element 324 is imbibed within the core 322. In other instances, the pores of the core 322 are filled by dissolving an elastomer in a solvent suitable to create a solution with a viscosity and surface tension that is appropriate to partially or fully flow into the pores of the core 322. The core 322 having an expanded fluoropolymer elongated body allows the solvent to evaporate, leaving the elastomer or elastomeric copolymer behind.

In an embodiment, a method of filling at least a portion of the pores of the core 322 includes the steps of delivering the filler via a dispersion to partially or fully fill the pores. In another embodiment, the pores of the core 322 may be filled by polymerizing the porosity-reducing element 324 within the pores of the core 322 by first filling the pores with a prepolymer of the elastomer and then at least partially curing the elastomer.

Figure 6:
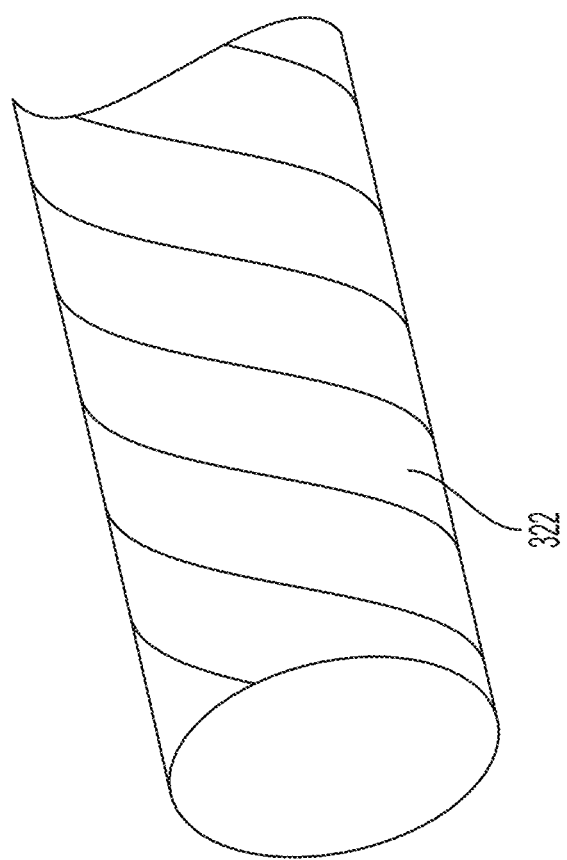
FIG. 6 is an illustration of a portion of a suture device in accordance with an embodiment.

FIG. 6 is an illustration of a portion of an example suture device in accordance with an embodiment. As shown in FIG. 6, a core 322 is formed of a bunched or twisted fluoropolymer or fluoropolymer composite (as is described in detail above). The bunched or twisted core 322 may have uniform or non-uniform ridges to form a flexible cord, as discussed in detail above. The bunched or twisted core 322 may allow for controlled distribution of a strength for alignment with the core.

To form the bunched or twisted core 322, a flat sheet of film is radially gathered, bunched, or twisted together it to produce a cord-like structure of the bunched or twisted core 322 having a more uniform diameter.

Figure 7:
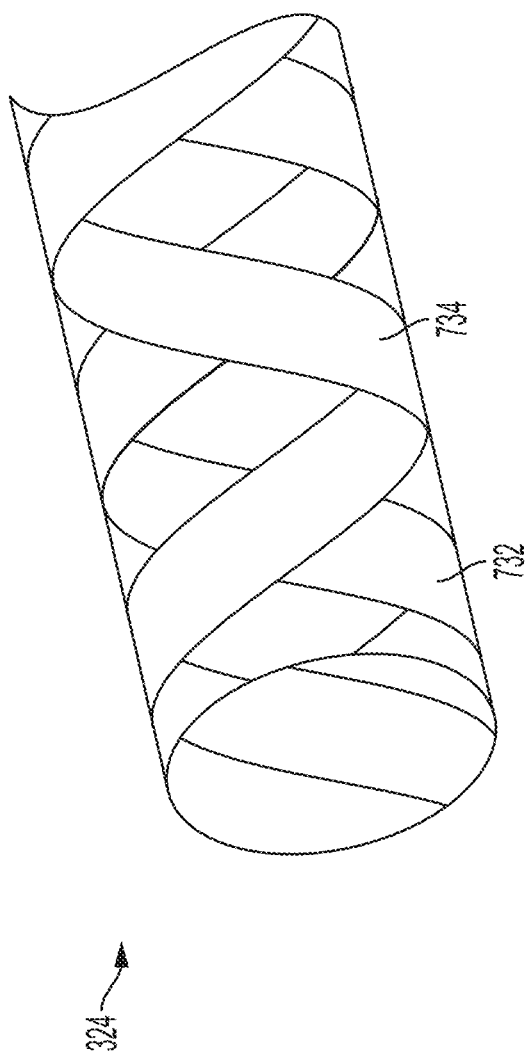
FIG. 7 is an illustration of a portion of a suture device in accordance with an embodiment.

FIG. 7 is an illustration of a portion of an example suture device in accordance with an embodiment. As shown in FIG. 7, a porosity-reducing element 324 is formed of a first portion 732 and a second portion 734. The first portion 732 and the second portion 734 may be braided together along a length of a flexible cord. In certain instances, the first portion 732 and the second portion 734 are wound or braided in opposite directions. In these instances, when the first portion 732 and the second portion 734 are arranged with a flexible cord, the first portion 732 and the second portion 734 may tighten as the flexible cord lengthens. The first portion 732 and the second portion 734 may allow for controlled distribution of a strength for alignment with the core.

Figure 8:
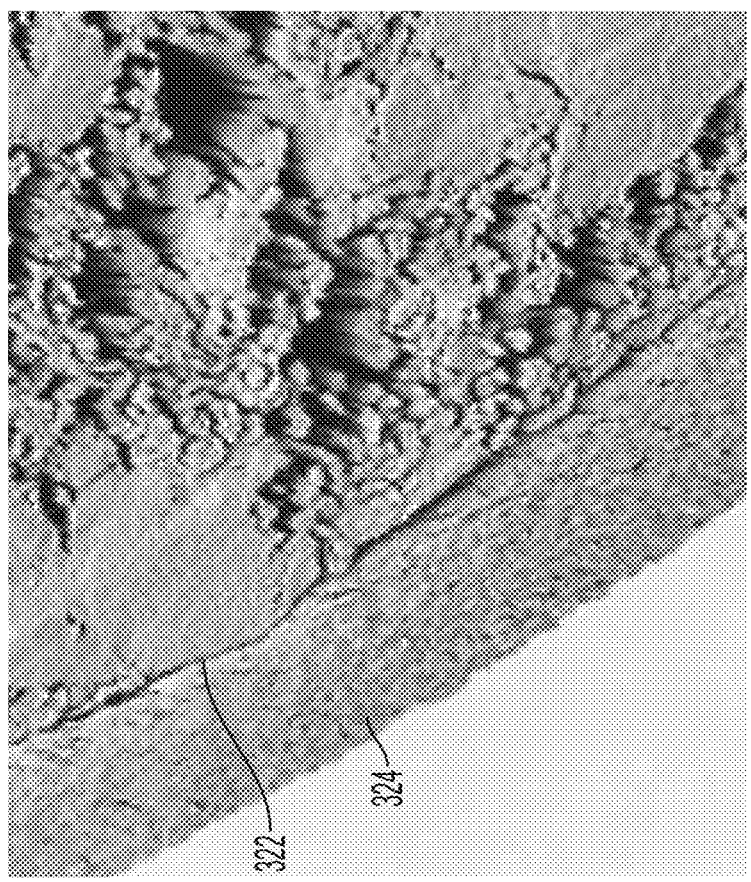
FIG. 8 is a scanning electron microscope (SEM) image of a flexible cord of a suture device in accordance with an embodiment.

FIG. 8 is a scanning electron microscope (SEM) image of an example cord 102 of a suture device in accordance with an embodiment. FIG. 8 shows a cross-section of the example cord 102, which has been reinforced by wrapping a core 322 with a porosity-reducing element 324. In certain instances, the core 322 is formed of polytetrafluoroethylene (PTFE) or expanded Polytetrafluoroethylene (ePTFE). The porosity-reducing element 324 may be an ePTFE, TFE-PMVE copolymer or another similar material that maintains the flexibility and strength of the core 322. The core 322 may be a porous structure with the porosity-reducing element 324 being configured to cover the core 322 and lessen the opportunity for calcification. In addition, the core 322 may be flexible with the porosity-reducing element 324 maintaining the flexibility of the core 322 such that the cord 102 is configured to mimic the flexibility of the natural chordae tendineae.

Figure 9B:
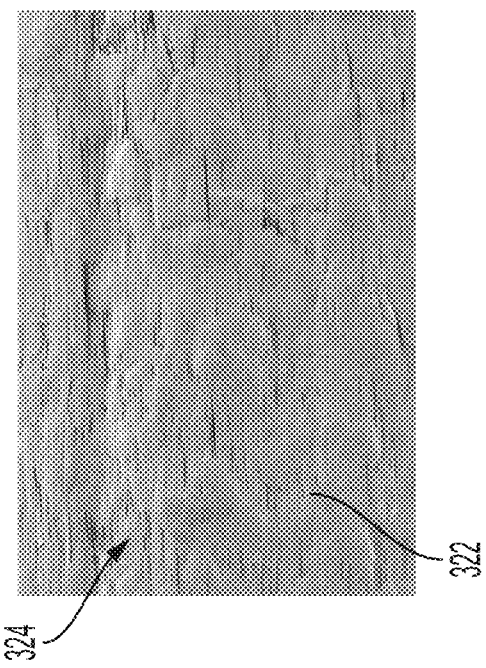
FIG. 9B is a scanning electron microscope (SEM) image of a film having a microstructure that is less porous or tighter than the microstructure of the embodiment of FIG. 9A, in accordance with an embodiment.
Figure 9A:
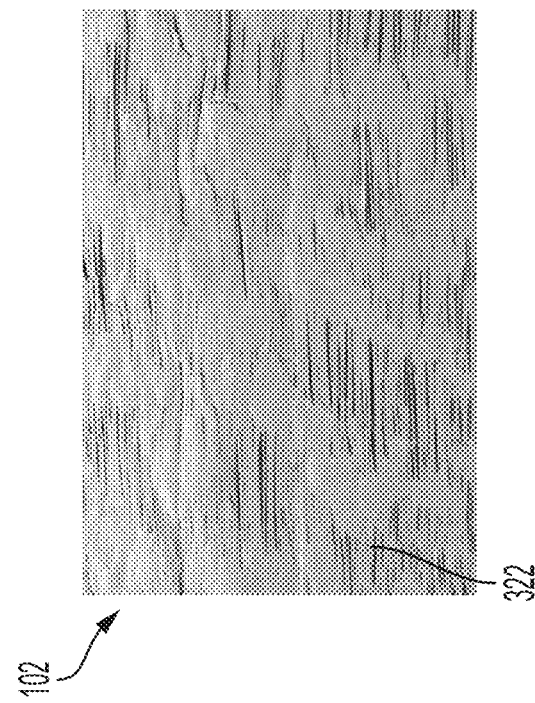
FIG. 9A is a scanning electron microscope (SEM) image of a core of a flexible cord of a suture device showing a more open microstructure than the microstructure of the embodiment of FIG. 9B in accordance with an embodiment.

FIG. 9A is a scanning electron microscope (SEM) image of a core of a flexible cord of a cord 102 showing a more open microstructure than the microstructure of the embodiment of FIG. 9B in accordance with an embodiment. As shown in FIG. 9A, a cord 102 includes a core 322, which is a porous structure. FIG. 9B is the flexible cord 102 of FIG. 9A after imbibing of a porosity-reducing element 324 (e.g., TFE-PMVE copolymer) to fill or cover the pores of the core 322. In certain instances, the flexible cord 102 may be coated, dipped, or wrapped or wrapped with the porosity-reducing element 324 to fill or cover the pores of the core 322. The cord 102 having pores that are covered, coated, or imbibed lessens the opportunity for calcification.

FIG. 10 is an illustration of a patient's heart with chordae tendineae, papillary muscles, mitral valve leaflets and suture devices in accordance with an embodiment. FIG. 10 shows the left side of the patient's heart 1000 which includes the aortic arch 1004, left atrium 1006, left ventricle 1008, with the mitral valve 1010 located between the left atrium 1006 and the left ventricle 1008. The chordae tendineae 1002a-g are attached to the leaflets of the mitral valve 1010 on one end, and papillary muscles 1012 in the left ventricle 1008 on the other end. The leaflets of the mitral valve 1010 (and tricuspid valve) are thin, diaphanous structures that rely on a system of the chordae tendineae 1002a-g to maintain competence of the valve in the loaded condition. These chordae tendineae 1002a-g attach the papillary muscles to the valve leaflets.

Stretched, ruptured, or broken chordae tendineae 1002a-g may alter functionality of the leaflets of the mitral valve 1010. In these instances, for example, the mitral valve 1010 may no longer fully coapt or close. As a result, blood can flow from the left ventricle 1008 back into the left atrium 1006 (e.g., mitral regurgitation). A transcatheter delivery approach and implantation of a cord 102, as discussed in detail above, for chordae tendineae replacement or repair can reduce morbidity and mortality risk.

Figure 11:
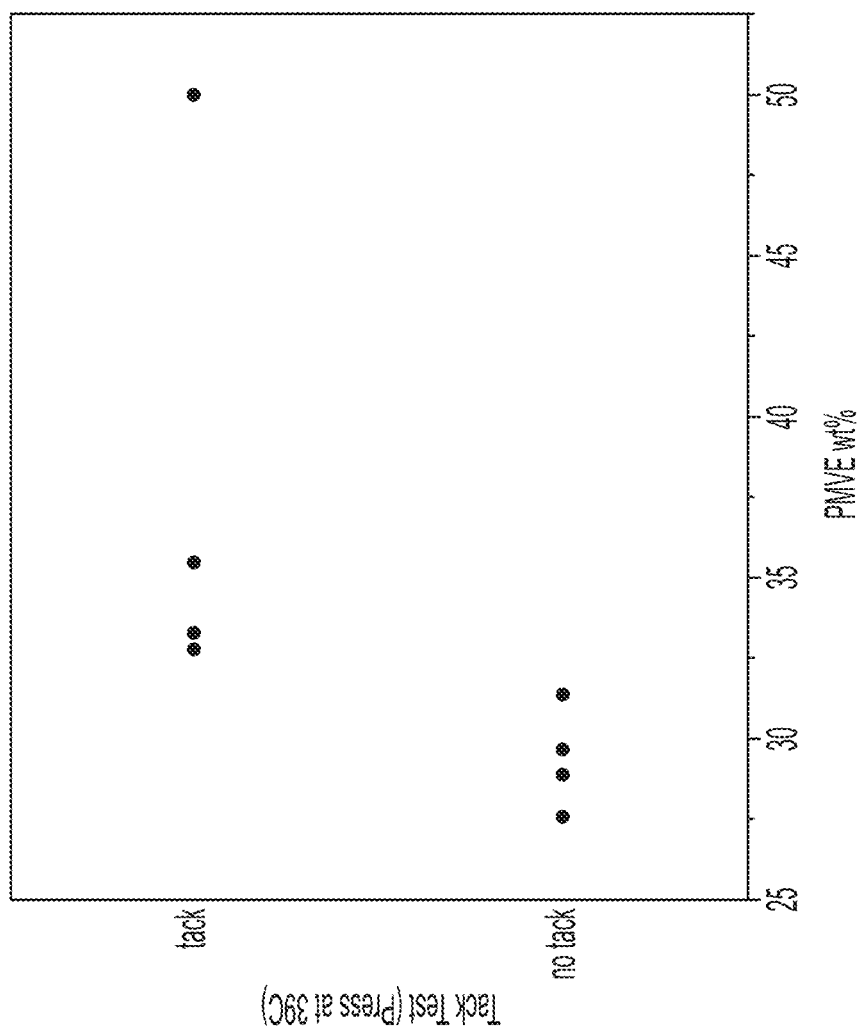
FIG. 11 is a chart of results of the tack test on various compositions of the TFE-PMVE films in accordance with embodiments.

FIG. 11 is a graph of results of the tack test on various compositions of the TFE-PMVE films. It is noted that a pair of TFE-PMVE films having a weight percent perfluoromethyl vinyl ether that is greater than 27 presents a positive tack result. No tack is found for a TFE-PMVE composition having equal to or less than about 27 weight percent perfluoromethyl vinyl ether.

In accordance with embodiments, the cord 102 would pass a tack test as provided herein. The tack test assesses the resistance of a cord 102, as discussed in detail above to stick to another surface. In accordance with the test of degree of tackiness of various compositions of TFE-PMVE copolymer, a number of pairs of TFE-PMVE films, each member of the pair comprising similar weight percent of perfluoromethyl vinyl ether and respective weight percent tetrafluoroethylene, were provided and placed in direct contact with each other. The respective pair of TFE-PMVE films were then sandwiched between polyimide films and pressed in a Model M Carver press (Carver Laboratory Press, Wasbash Indiana USA) at 39° C., 200 psi for 15 minutes. After 15 minutes, the pairs of TFE-PMVE films were removed from the press and the polyimide films were removed. The pair of two TFE-PMVE films were then separated from each other, if there was no adherence between the two TFE-PMVE films and no force was required to separate the two TFE-PMVE films, the TFE-PMVE composition was determined to have "no tack". A pair of two TFE-PMVE films that required force to separate the two TFE-PMVE films from each other were determined to have "tack". It is appreciated that a cord so modified with the above treatments will exhibit similar results related to tack.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A suture device comprising:
a cord that is flexible and elongated defining a length, a first end, and a second end opposite the first end, the cord including a core extending from the first end to the second end, the cord further including a composite film including a first portion helically wrapped around the core in a first direction and a second portion helically wrapped around the core in a second direction opposite to the first direction along the length of the cord.

2. The suture device of claim 1, further comprising a first attachment element at the first end of the cord configured to attach to a first location at a first tissue; and a second attachment element at the second end of the cord configured to attach to a second location at a second tissue.

3. The suture device of claim 1, wherein the core has a porous surface.

4. The suture device of claim 3, wherein the composite film is a porosity-reducing element positioned on at least a portion of the core.

5. The suture device of claim 4, wherein the composite film covers the porous surface of the core.

6. The suture device of claim 4, wherein the composite film is a non-permeable film.

7. The suture device of claim 4, wherein the composite film includes an ePTFE film having a micro-structure that has smaller pores than a microstructure of the surface of the core.

8. The suture device of claim 1, wherein the composite film is coupled to a portion of the core.

9. The suture device of claim 1, wherein the core is formed of a twisted fluoropolymer or fluoropolymer composite.

10. The suture device of claim 9, wherein the core is formed of a flat sheet of film that is radially gathered, bunched, or twisted together.

11. The suture device of claim 1, wherein composite film includes an elastomer TFE-PMVE copolymer, elastomeric material TFE-PMVE copolymer, or non-elastomeric TFE-PMVE copolymer coating on the portion of the core rendering the surface of the core at the portion of the core non-porous.

12. The suture device of claim 1, wherein the composite film includes an elastomer, elastomeric material, or non-elastomeric TFE-PMVE copolymer imbibed into the pores of the portion of the core rendering the surface of the core at the portion of the core non-porous.

13. The suture device of claim 1, wherein the composite film includes an elastomer or elastomeric material imbibed into the pores of the portion of the core further including a non-elastomeric TFE-PMVE copolymer coating on the portion of the core rendering the surface of the core at the portion of the core non-porous.

14. The suture device of claim 1, wherein the composite film includes an elastomer, elastomeric material, or non-elastomeric TFE-PMVE copolymer coating on and imbibed into the pores of the portion of the core rendering the surface of the core at the portion of the core non-porous.

15. A suture device comprising:
a cord that is flexible and elongated defining a length, a first end, and a second end opposite the first end, the cord including a core extending from the first end to the second end, the core being formed of a twisted fluoropolymer or fluoropolymer composite and having a porous surface, the cord further including a porosity-reducing element including a first portion helically wrapped around the core, wherein the porosity-reducing element include a second portion helically wrapped around the core in an opposite direction relative to the first portion of the porosity-reducing element.

16. The suture device of claim 15, wherein the core is formed of a flat sheet of film that is radially gathered, bunched, or twisted together.

17. The suture device of claim 15, wherein the porosity reducing element is a composite film.

18. The suture device of claim 17, wherein the composite film is a non-permeable film.

19. The suture device of claim 18, wherein the composite film includes an ePTFE film having a micro-structure that has smaller pores than a microstructure of the surface of the core.

20. A suture device comprising:
a cord that is flexible and elongated defining a length, a first end, and a second end opposite the first end, the cord including a core extending from the first end to the second end, the core being formed of a twisted fluoropolymer or fluoropolymer composite and having a porous surface, the cord further including a porosity-reducing element including a first portion helically wrapped around the core, wherein the porosity reducing element is a composite film, wherein the composite film is a non-permeable film, and wherein the composite film has a micro-structure that has smaller pores than a microstructure of the surface of the core.

\* \* \* \* \*